(12) United States Patent
Kurowski et al.

(10) Patent No.: US 9,182,326 B2
(45) Date of Patent: Nov. 10, 2015

(54) DEVICE AND METHOD FOR FILTERING BLOOD

(75) Inventors: Dirk Kurowski, Gevelsberg (DE); Dirk Osterloh, Unna (DE); Ying Yu, Dortmund (DE)

(73) Assignee: Boehringer Ingelheim Microparts GmbH, Dortmund (DE)

( * ) Notice: Subject to any disclaimer, the term of this patent is extended or adjusted under 35 U.S.C. 154(b) by 65 days.

(21) Appl. No.: 14/006,996

(22) PCT Filed: Mar. 23, 2012

(86) PCT No.: PCT/EP2012/055264
§ 371 (c)(1),
(2), (4) Date: Nov. 19, 2013

(87) PCT Pub. No.: WO2012/127050
PCT Pub. Date: Sep. 27, 2012

(65) Prior Publication Data
US 2014/0134595 A1 May 15, 2014

(30) Foreign Application Priority Data
Mar. 24, 2011 (EP) .................................... 11002441

(51) Int. Cl.
*G01N 1/40* (2006.01)
*B01L 3/00* (2006.01)

(52) U.S. Cl.
CPC .......... *G01N 1/4005* (2013.01); *B01L 3/50273* (2013.01); *B01L 3/502715* (2013.01); *B01L 3/502753* (2013.01); *B01L 3/502723* (2013.01); *B01L 2200/027* (2013.01); *B01L 2300/0681* (2013.01); *B01L 2300/0816* (2013.01); *B01L 2300/0887* (2013.01); *B01L 2400/0406* (2013.01); *B01L 2400/0487* (2013.01)

(58) Field of Classification Search
CPC .................. B01L 2300/0681; B01L 2200/027; B01L 2400/0406; B01L 3/502753; G01N 1/4005; G01N 2001/4088
See application file for complete search history.

(56) References Cited

U.S. PATENT DOCUMENTS

| 6,071,294 A * | 6/2000 | Simons et al. ................ 606/181 |
| 7,524,462 B2 * | 4/2009 | Leonard et al. ............... 422/417 |
| 7,736,907 B2 | 6/2010 | Blankenstein et al. |
| 2004/0228770 A1 | 11/2004 | Gandhi et al. |
| 2007/0269893 A1 * | 11/2007 | Blankenstein et al. ........... 436/2 |
| 2014/0134595 A1 | 5/2014 | Kurowski |

FOREIGN PATENT DOCUMENTS

| EP | 0977032 A1 | 2/2000 |
| WO | 2005119211 A1 | 12/2005 |
| WO | 2012127050 A2 | 9/2012 |

OTHER PUBLICATIONS

International Search Report and Written Opinion for PCT/EP2012/055264 mailed Nov. 12, 2012.

* cited by examiner

*Primary Examiner* — Paul Hyun
(74) *Attorney, Agent, or Firm* — Michael P. Morris; Mary-Ellen M. Devlin

(57) ABSTRACT

The invention relates to a device and a method for filtering a liquid sample, wherein first capillary-driven filtration occurs and, after initial filling, pressure-operated filtration is performed by applying a vacuum or a positive pressure.

6 Claims, 2 Drawing Sheets

DEVICE AND METHOD FOR FILTERING BLOOD

The present invention relates to devices and methodologies for filtering a liquid sample, particularly blood.

The present invention is concerned with the filtration of a liquid sample. This is preferably a biological sample or sample liquid, particularly blood or the like. In particular, the present invention relates to the filtration of a particle-containing solution (suspension) such as blood or some other human or animal body fluid.

The present invention is concerned particularly with fluidic devices which contain or form a microfluidic system. The following remarks therefore preferably apply to devices in which capillary forces are at work and are important or crucial to the operation, in particular.

Devices are known in which blood is filtered by means of a membrane. The filtrate or permeate is received in a chamber that flatly adjoins the membrane and is drained off laterally through a channel. Devices of this kind for blood separation are known, for example, from WO 2005/119211 A1 and WO 2009/106331 A2.

The blood separation can be accelerated or assisted by the application of pressure, particularly the application of a negative pressure or vacuum. EP 1 421 993 A1 discloses a device for separating blood in which a carrier consisting of a non-woven transporting fabric, e.g. made of fibreglass, is provided with a non-woven separating fabric in a blood separating area. The separating fabric forms a filter for separating off blood components. The blood separation is carried out by capillary forces, while a negative pressure may, for example, be applied in an auxiliary capacity. However, there is no technical instruction for creating the negative pressure. After the separation of the blood, the blood plasma that has been separated off is removed from the non-woven transporting fabric by squeezing out. If required, the region of the carrier with the separating fabric may be separated from the remainder of the carrier in order to prevent any possible contamination of the blood plasma by blood cells. A disadvantage here is that there is relatively undefined and slow separation of the blood and conveying of the separated plasma into a non-woven fabric. A further disadvantage is that a separate device is required for squeezing out the fabric in order to remove the separated blood plasma.

The problem on which the present invention is based is to provide a device and a method for filtering a liquid sample such as blood, which allows optimised or accelerated filtration and/or a simple construction.

The above problem is solved by a devise and/or methodologies disclosed herein.

In one aspect of the present invention, during the filtering of a sample through a membrane, first of all the filtration is carried out (only) in capillary-driven manner, i.e. driven by capillary forces, until the filtered sample reaches or partly fills a fluidic system associated with the membrane for draining off, and only then is a negative or positive pressure used to accelerate the filtration or promote further filtration, i.e. pressure-operated filtration is then carried out. For this purpose a conveying device is used, in particular, which only produces or uses a negative or positive pressure to accelerate the filtration or promote further filtration after the filtered sample has reached or partly filled the fluidic system. In this way, various advantages are obtained.

The initially capillary-driven filtration can prevent or at least minimise air inclusions and air bubbles.

At the start of filtration or during capillary-driven filtration there is, however, a slight risk of haemolysis (unwanted wetting or destruction of cells such as blood cells during filtration).

The initially purely capillary-driven filtration allows an optimum fluidic seal to be formed between the gas exchange or the entry of gases from outside, particularly between the membrane used for the filtering and the fluidic system downstream thereof, so that, in particular, there is no need for an airtight connection or complex connecting means for gastight connecting of the filtration membrane with the associated carrier or fluidic system.

The subsequent pressure-operated filtration allows the filtration to be speeded up compared with the purely capillary-driven filtration, thus enabling particularly rapid filtration or high volume flows.

The pressure-operated filtration allows greater reproducibility, as the flow is determined and may be controlled or even regulated by the pressure difference or the level of negative or positive pressure acting thereon.

In the pressure-operated filtration, native or untreated materials, particularly hydrophobic materials, may be used for the carrier or the fluidic system, even when filtering hydrophilic samples. This helps to make manufacture easy and inexpensive.

According to one alternative embodiment the membrane rests only loosely on a carrier that forms the fluidic system, or on its cover. This results in a very simple design or manufacture. In particular, this is possible because an initial fluidic seal is enabled or achieved by the capillary filling during the initial capillary-driven filtration.

Preferably, the negative or positive pressure for the pressure-operated filtration is limited to a maximum of 100 mPa, particularly to approximately 50 mPa or less. In this way it is possible to prevent the fluidic seal, in particular, between the membrane on the one hand and the carrier or the fluidic system or the cover for the carrier on the other hand from being overstressed or becoming leaky.

Particularly preferably, the filtered sample is drained off on a flat side of the membrane through a receiving opening of the fluidic system, the receiving opening preferably being arranged at least substantially centrally or in the middle underneath the membrane. This helps with the preferably particularly circumferential or annular fluidic seal by means of the filtered sample.

Preferably, the membrane lies at least substantially flat on the carrier and/or its cover. As a result the dead volume for the filtered sample underneath the membrane can be minimised or almost totally prevented.

According to another aspect of the present invention the membrane may be directly connected to the carrier that forms the fluidic system and/or may be accommodated in a recess thereof, when the filtered sample is drained off under the membrane, preferably perpendicularly to the flat side or through the carrier, particularly through an opening in the carrier. This allows the construction to be very simple and compact, while in particular there is no need for an external or additional provision of a feed device or receiving device for the sample.

In another aspect of the present invention the device preferably comprises a feed device for the sample which is in capillary contact with the membrane. The feed device is funnel-shaped, for example, and feeds the sample that is to be filtered, particularly by capillary forces, in direct contact with the membrane. The feed device is arranged, in particular, in a receiving device for the sample or is formed thereby, while the membrane, in turn, is preferably connected to the receiving device at its edges and/or circumferentially. This allows a very simple structure with reliable feeding of the sample to the membrane, while in particular there is no need for a hydrophilic wall or coating of the feed device or receiving device, even when filtering a hydrophilic sample, as the sample is conveyed directly to the membrane by capillary or direct contact through the feed device.

The above-mentioned aspects of the present invention and the aspects of the present invention that arise from the following description and claims may be implemented independently of one another or in any desired combination.

Further advantages, features, properties and aspects of the present invention will become apparent from the claims and the following description of preferred embodiments by reference to the drawings, wherein:

In the Figures, the same reference numerals are used for identical or similar parts, where corresponding or comparable properties and advantages are obtained, even if there is no repetition of the description.

Figure 1:
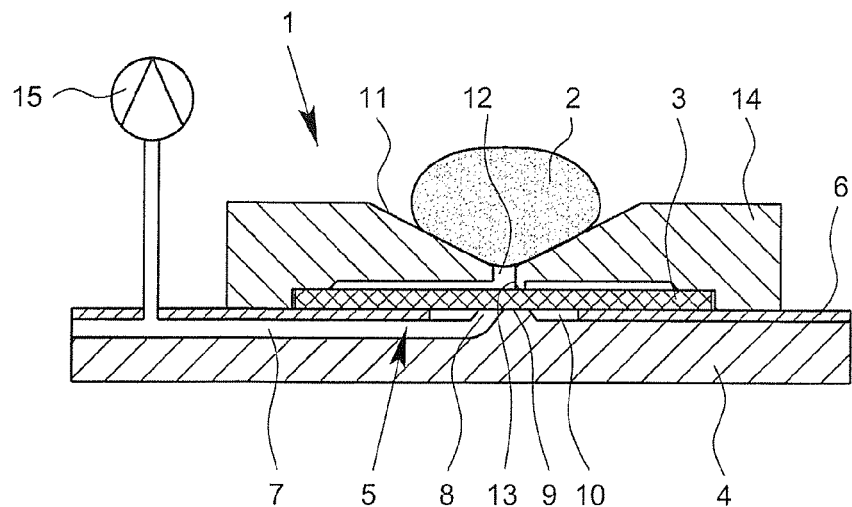
FIG. 1 shows a schematic section through a proposed device according to a first embodiment.

FIG. 1 shows, in schematic section, a proposed device 1 for filtering a liquid sample 2. In particular, the sample 2 is a particle-containing solution or suspension.

Particularly preferably, it is a biological sample 2. In the embodiment shown it is, in particular, blood or some other human or animal body fluid. However, other liquids or suspensions or the like may also be filtered as samples 2.

The device 1 preferably comprises a membrane 3 or other separating device for filtering the sample 2 or for separating ingredients or particles from the sample 2.

The membrane 3 is preferably constructed or formed as described in WO 2009/106331 A2, which is hereby incorporated by reference as a supplementary disclosure.

By the term "membrane" is meant, in particular, a flat filter element that is suitable for filtering a liquid sample 2 in the sense meant here, particularly blood or the like, particularly for separating blood cells and/or plasma.

The membrane 3 may, if required, also be of multi-layered construction and/or of more or less open-pored design. It may also be a suitable composite material.

In particular, a plurality of membranes or filter elements may be layered directly over one another.

The device 1 comprises a carrier 4 that forms or comprises a fluidic system 5. In particular, the fluidic system 5 is at least partly or completely formed by or in the carrier 4, optionally together with a cover 6.

The carrier 4 preferably has an at least substantially plate-shaped and/or rigid outer shell and is particularly preferably made of plastics, particularly by injection moulding.

The device 1 preferably comprises a cover 6 associated with the carrier 4, which preferably at least partly covers the fluidic system 5. In particular, the cover 6 covers depressions, channels or the like formed in the carrier—preferably in fluid-tight and particularly also gas-tight manner, at least partially, which form at least parts of the fluidic system 5.

The cover 6 is preferably at least substantially smooth, planar, elastically deformable and/or film-like in construction. In particular it is a plastic film or the like.

The cover 6 is preferably arranged or mounted on a flat side of the carrier 4, for example by adhesive bonding, sealing, particularly heat-sealing, welding or the like.

In the embodiment shown the device 1 or the carrier 4 or the fluidic system 5 preferably comprises a receiving channel 7 with a receiving opening 8 for the preferably filtered sample 2 or the permeate.

In the first embodiment shown in FIG. 1 the carrier 4 preferably has an elevated area 9 which is particularly preferably in direct contact with the membrane 3 or on which the membrane 3 preferably rests directly.

The receiving opening 8 or the receiving channel 7 preferably opens towards the membrane 3 in this elevated region 9 of the carrier 4. In other words, the receiving channel 7 begins, in particular, in the elevated region 9.

The receiving channel 7 is preferably formed by a corresponding groove, channel or other recess in the carrier 4 and, in the embodiment shown, preferably extends along the surface or flat side of the carrier 4 facing the membrane 3. This makes it very easy to manufacture the carrier 4 and the grooves, channels or the like by injection moulding, in particular.

The cover 6 covers the carrier 4 or its surface or flat side facing the membrane 3, preferably at least substantially completely, in particular the receiving channel 7, so that the receiving channel 7 or its receiving opening 8 opens at least substantially only centrally underneath the membrane 3 towards the membrane 3 or generally. By the term "centrally" is meant here, in particular, an at least substantially central arrangement. Alternatively or additionally, however, this may also mean that only a single receiving opening 8 is provided for draining off the filtered sample 2 or the permeate.

In the embodiment shown in FIG. 1 the receiving channel 7 runs to the left, starting from the receiving opening 8. The receiving channel 7 is covered by the cover 6. Then other channels, cavities, such as a reservoir or similar of the fluid system 5 may be connected to the receiving channel 7, for example for manipulating or investigating the filtered sample 2, particularly blood plasma.

In the embodiment shown, the cover 6 preferably extends to below the membrane 3, particularly from all sides or circumferentially. Particularly preferably, the cover 6 forms an annular abutment area around the receiving opening 8 or the elevated region 9.

In the embodiment shown, the membrane 3 lies, preferably at least substantially over its full surface or uniformly, on the elevated region 9 and around the outside of the carrier 4 or its cover 6. In this way a very small or even negligible dead volume for the filtered sample 2 can be formed on the delivery side of the membrane 3.

Between the elevated region 9 and the cover 6 laterally adjoining it there is ideally or preferably a certain distance, so that preferably an annular region 10 is formed. This is filled by the filtered sample 2 and is preferably fluidically connected to the receiving opening 8 or the receiving channel 7. This results in optimised drainage of the filtered sample 2 under the membrane and/or optimum fluidic sealing against the ingress of air.

The filtered sample 2 or the permeate is received through the receiving opening 8 from the receiving channel 7 or fluidic system 5 and drained away, particularly for further manipulation or investigation, for delivery to another device or for external examination or the like. FIG. 1 shows the device 1 and the sample 2, however, in a state before the start of the capillary-operated filtration or before the sample 2 flows or diffuses onto and into the membrane 3.

The device 1 preferably comprises a feed device 11 for feeding the sample 2 that is to be filtered to the membrane 3. The feed device 11 is preferably of funnel-shaped construction in the embodiment shown or is provided with a funnel-shaped region.

The feed device 11 is preferably embodied to be in capillary contact and/or direct contact with the membrane 3, in order to supply the sample 2 to the membrane 3 itself when the material that forms the feed device 11 or its surface can only be poorly wetted or virtually not wetted at all by the sample, for example because the feed device 11 or its material is hydrophobic and the sample 2, by contrast, is hydrophilic.

In the embodiment shown, the sample 2 is conveyed by the feed device 11 preferably onto the centre or middle of the membrane 3 and/or is passed through a central or middle feed opening 12 and/or a feed portion 13 extending directly into the vicinity of or onto the membrane 3, in order to produce the preferred direct or capillary contact with the membrane 3 for the sample 2. The feed portion 13 may for example be a capillary tube, a notch, a column structure and/or some other suitable structure.

The device 1 preferably comprises a receiving device 14 for receiving the sample 2 that is to be filtered and/or for securing the membrane 3. In the embodiment shown the membrane 3 is preferably connected to the receiving device 14 in fixed or non-releasable manner, particularly in an encircling edge portion, for example by welding, adhesion, clamping and/or by any other suitable method. In the embodiment shown the receiving device 14 comprises, in particular, a corresponding receiving opening or recess for the membrane 3.

In the embodiment shown the feed device 11 is arranged in the receiving device 14 and/or is formed thereby or embodied in one piece therewith. However, other design solutions are also possible.

The construction of the feed device 11 so that it is in direct and/or capillary contact with the membrane 3 for the sample 2 represents a special aspect of the present invention which can be implemented irrespective of the proposed combination of capillary force-operated and pressure-operated filtration.

Particularly preferably, purely capillary-driven filtration or filling takes place at first or initially. Thus the sample 2 penetrates into the membrane 3 as a result of (only) capillary forces and penetrates through this membrane, while in particular solid ingredients of the sample 2 such as cells, at least of a certain size, are retained by the membrane 3, i.e. filtered out of the sample 2.

As the sample 2 is fed in it may optionally spread over the flat inlet side of the membrane 3.

The membrane 3 preferably has a thickness and/or structure such that the sample 2 can flow into the areal extent of the membrane 3 within the membrane 3. This flow is also referred to as "transverse flow" in the present invention.

In the embodiment shown the transverse flow in the membrane 3 is very important as the membrane 3 is preferably at least substantially placed with its entire surface on the underlying cover 6 in the outer annular region, which crucially results in the preferred small dead volume, but is associated with a lower throughput or lower filter performance and/or requires, in particular, the above-mentioned transverse flow of the sample 2 in the membrane 3.

The filtered sample 2 fills the interstices, which are preferably very small in the embodiment shown, between the membrane 3 and the carrier 4 or the cover 6, thus achieving a particularly air-tight seal relative to the environment. This seal is referred to as a "fluidic seal" for short in the present invention.

Particularly in the relatively slow capillary force-driven filtering of the sample 2 and the subsequent filling of the cavities, interstices and the like adjoining the membrane 3 on the drainage side, any air contained therein is displaced. For example, the annular region 10, if present, is preferably completely filled with no inclusion of air or air bubbles.

Finally, the filtered sample 2 reaches the fluidic system 5, in this case the receiving opening 8 and the receiving channel 7, and, depending on the capillary forces in action, may optionally begin to fill the fluidic system 5 as well. However, this is not absolutely necessary.

After the initial capillary-driven filtration and/or filling as described above, a pressure-driven filtration takes place, particularly preferably, by the application of a negative or positive pressure, thereby continuing the filtration and/or accelerating it compared with the capillary-driven filtration and optionally even making further filtration possible.

To produce the negative or positive pressure the device 1 preferably has a conveying device 15 associated with it. The conveying device 15 may be, for example, a vacuum pump, negative pressure pump or the like. The conveying device 15 may be a separate device. However, the conveying device 15 may also form part of the device 1 or may be integrated therein.

A negative or positive pressure for accelerating the filtration and/or for the further filtration is preferably only produced or applied after the filtered sample 2 has reached or partially filled the fluidic system 5. This can be done, for example, by detecting whether the sample 2 has reached or partly filled the fluidic system 5 and only then switching the conveying device 15 on or off or opening or closing a corresponding valve or closing a corresponding vent. For example, this may be done by means of a corresponding detecting device (not shown) or by the fact that the filtered sample 2 itself closes a vent opening or the like, for example after partially filling the fluidic system 5. Alternatively or additionally, the production of the negative or positive pressure for the pressure-operated filtration may also take place after a predetermined time, for example after the addition of the sample 2 to the device 1. This can be carried out using a corresponding time control or the like.

The further filtration is pressure-operated, i.e. using negative or positive pressure, which may serve to assist or accelerate the filtration or even make filtration possible in the first place.

The fluidic seal presents the unwanted penetration of air or other gas, particularly during filtration under negative pressure.

In particular, it is even possible according to the invention to place the membrane 3—optionally together with the feed device 11 and/or receiving device 14—only loosely on the carrier 4 or on its cover 6. The fluidic seal then provides the desired seal relative to the environment. In this way it is possible to do without a gas-tight connection of the feed device 14 to the carrier 4 or cover 6 that would otherwise be essential.

The negative or positive pressure that is used or comes into effect during filtration is preferably limited to a maximum of 100 mPa, particularly approximately 50 mPa or less. In this way it can be ensured that the fluidic seal is not over-stressed. In particular, with a limit of this kind it is possible to ensure or make certain that the capillary forces or diffusion forces that provide the fluid seal are greater than the pressure forces exerted.

The fluidic seal is assisted by the, particularly preferably, direct placement of the membrane 3 on the carrier 4 or its cover 6, as this ensures direct contact with the sample 2. In particular, all the interstices on the delivery side or permeate side towards the carrier 4 or its cover 6 are thus minimised and/or reliably filled. However, the membrane 3 may theoretically also be somewhat spaced from the carrier 4 or its cover 6, preferably only by a small amount.

The proposed combination of the initially only capillary-driven filtration or initial filling with the subsequent pressure-operated or pressure-assisted filtration, in which the filtration is accelerated or assisted (or carried out by means of negative or positive pressure) leads to various advantages.

The initial capillary filling has the result, or helps to ensure, that the filtered sample 2, particularly the plasma, is free from air bubbles and/or air inclusions in the device 1, particularly in the membrane 3 and/or in interstices adjoining it, are avoided.

The proposed combination allows a "loose" connection or placement or, for example, a non-gas-tight connection between the actual sample receptacle such as the membrane 3, the feed device 11 and/or receiving device 14, on the one hand, and the receptacle for the filtered sample 2 or the plasma, such as the carrier 4, the fluidic system 5 and/or the cover 6, on the other hand.

The filtration is highly reproducible as the flow rate is critically determined by the pressure difference, i.e. the negative pressure or positive pressure in play, and can be controlled or regulated as necessary.

A high filtration performance and high flow rates can be achieved. The entire yield or total amount of filtered sample 2 or blood plasma delivered cannot normally be increased, however, as this volume is usually determined primarily or exclusively by the capacity of the membrane 3, as the membrane 3 will finally "clog up" at the end of filtration.

The proposed combination leads to a low risk of haemolysis, as particularly at the beginning the capillary-driven filtration avoids undesirable destruction of cells such as blood cells or the like. During further filtration the risk of haemolysis even during pressure-operated filtration is no longer as great.

The proposed combination makes it possible to use only one hydrophilic membrane 3, for example, with a hydrophilic liquid. The other structures may for example be made from native or untreated or hydrophobic plastics or glass and/or in particular need not be hydrophilic. The hydrophilic or hydrophilised membrane 3 in fact leads to sufficient or total wetting of the following structures such as the carrier 4 and/or the cover 6, particularly directly underneath the membrane 3, when there is corresponding contact on the drainage side. However, at least partial hydrophilisation of the other structures may also be advantageous in order to achieve faster wetting.

Further embodiments and variants of the proposed device 1 and proposed method will be explained in more detail hereinafter with reference to the additional figures. The previous remarks and explanations apply accordingly, in particular, even where they have not been repeated. In particular, corresponding or similar features or properties are also obtained.

Figure 2:
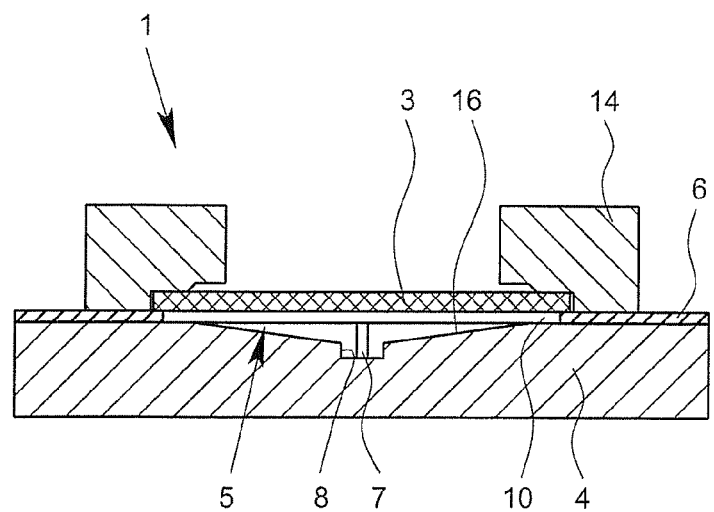
FIG. 2 shows a schematic section through a proposed device according to a second embodiment.
Figure 3:
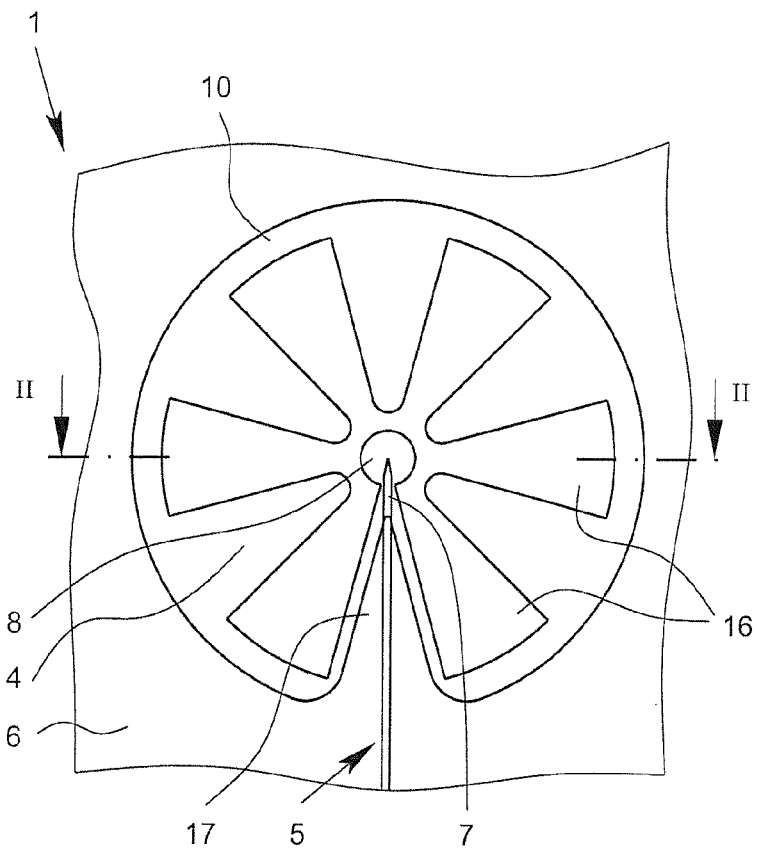
FIG. 3 shows a schematic plan view of a carrier of the device according to the second embodiment.

FIG. 2 shows, in schematic section, a second embodiment of the proposed device 1. FIG. 3 shows the device 1 according to the second embodiment in plan view, but shows only the carrier 4 with the cover 6.

In the second embodiment, a structure 16 for supplying the filtered sample 2, i.e. the permeate, to the receiving opening 8 or receiving channel 7 or fluidic system 5 is provided or formed underneath the membrane 3. The structure 16 is formed in particular by the carrier 4 or in the carrier 4.

The structure 16 particularly comprises grooves, depressions, channels, ramps or the like and/or is recessed or inclined, particularly at least substantially starting from the edge of the membrane 3 and/or radially and/or towards the receiving opening 8, in particular in order to convey the filtered sample 2 or the permeate from the outside inwards or towards the centre or towards the receiving opening 8. Particularly preferably, the structure 16 comprises a sector-like construction or a plurality of depressions, ramps or the like extending in a sector-like configuration, as can be seen particularly from the plan view in FIG. 3.

However, the structure 16 may additionally or alternatively comprise other elevations, columns, projections or the like which provide in particular fluidic contact with the membrane 3 located above.

In the second embodiment the feed device 11 has been omitted.

In the second embodiment the membrane 3 is in turn preferably connected in leak-tight manner, particularly welded, to the receiving device 14 at its edges and/or circumferentially.

The receiving device 14 is preferably of at least substantially annular configuration.

The receiving device 14 is preferably connected to the carrier 4 or its cover 6, although a gas-tight connection is not absolutely essential.

In the second embodiment the cover 6 preferably comprises an in particular tongue-like projection 17 which extends to the centre or receiving opening 8 underneath the membrane 3, as is apparent particularly from FIG. 3. The projection 17 covers the receiving channel 7, so that the receiving opening 8 opens at least substantially only centrally or only in the middle under the membrane towards the membrane 3. This central or middle drainage of the filtered sample 2 or of the permeate, particularly the blood plasma, leads to a particularly good fluidic seal.

With respect to a good fluidic seal, an annular region 10 is preferably formed circumferentially and/or along the edge of the membrane 3, under the membrane 3, in which the liquid sample 2 or the permeate is held by capillary forces. This is achieved by corresponding contact or a small spacing of the membrane 3 from the underlying carrier 4 or its cover 6. Preferably, the annular region 10 is very flat in cross section, i.e. its width or radial extent is substantially greater than its height. This contributes to a good fluidic seal.

In the second embodiment the structure 16 leads to better or faster drainage or removal of the filtered sample 2 or permeate over a larger surface under the membrane 3, thus enabling a higher filter performance and hence a higher throughput. However, this results in a higher dead volume under the membrane 3, or between the membrane 3 and the actual fluidic system 5 or receiving opening 8.

One advantage of the structure 16 or similar structures is that there is no need for any transverse flow in the membrane 3. In particular, it is therefore possible to use membranes 3 without transverse flow or with only a reduced transverse flow.

Figure 4:
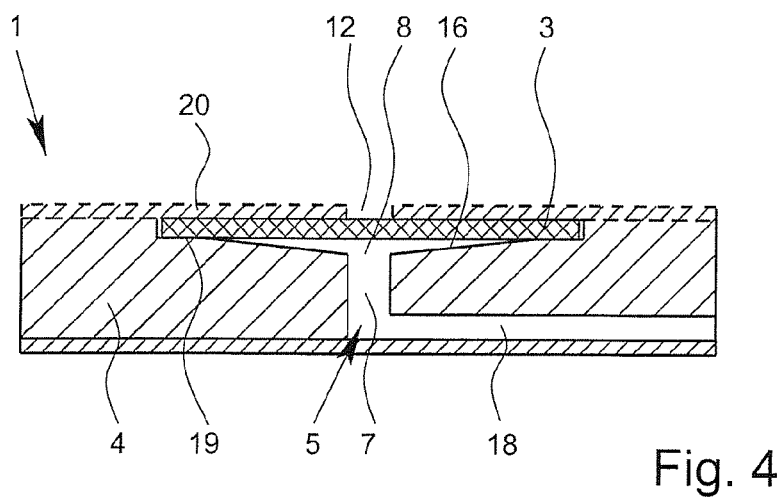
FIG. 4 shows a schematic section through a proposed device according to a third embodiment.

FIG. 4 shows in schematic section a third embodiment of the proposed device 1. Here, the receiving channel 7, at least the portion immediately adjacent to the receiving opening 8, extends transversely of the flat extent of the carrier 4 or the membrane 3 and/or preferably at least substantially perpendicular to the surface or flat side of the carrier 4. Particularly preferably, the receiving channel 7 is embodied or configured as an opening in the carrier 4, as there is no need for the receiving channel 7 or a groove or the like formed for this purpose in the carrier 4 to be covered by the cover 6 on the flat side of the carrier 4 facing the membrane 3.

In particular, adjoining the receiving channel 7 on the other flat side is another channel 18 of the fluidic system 5 which then extends parallel to the flat side, for example, and in particular is covered by the cover 6 arranged on this flat side. However, here too, other design solutions or arrangements are possible.

In the first embodiment the membrane 3 is preferably accommodated in a recess 19 of the carrier 3, as shown in FIG. 4. This is possible in particular because of the drainage of the filtered sample 2 onto the other side of the carrier 4 and/or by the passage of the receiving channel 7 at right angles to the main plane of extent of the membrane 3 and/or of the carrier 4, as there is no need for the receiving channel 7 or a groove or the like formed for this purpose in the carrier 4 to be covered by the cover 6 on the flat side of the carrier 4 facing the membrane 3.

The membrane 3 may be connected, particularly welded, to the carrier 4, particularly at the edges and/or circumferentially, particularly in the recess 19.

Alternatively or additionally, the membrane 3 may be covered at least partially, more particularly by a lid 20, preferably formed by a corresponding film or the like. The lid 20 or the film is then preferably provided with a corresponding feed opening 12 for receiving the sample 2. The lid 20 or film may secure or retain the membrane 3 on the carrier 4 as well, particularly in the recess 19, and/or may form a (sufficient) seal particularly at the edge.

The individual embodiments and individual features and aspects of the different embodiments may also be implemented in any desired combination with one another or independently of one another.

LIST OF REFERENCE NUMERALS

1 Device
2 Sample
3 Membrane
4 Carrier
5 Fluidic system
6 Cover
7 Receiving channel
8 Receiving opening
9 Elevated region
10 Annular region
11 Feed device
12 Feed opening
13 Feed portion
14 Receiving device
15 Conveying device
16 Structure
17 Projection
18 Channel
19 Recess
20 Lid

The invention claimed is:

1. A device (1) for filtration of a liquid sample (2), comprising:
 a membrane (3) for filtering the sample (2),
 a carrier (4) that forming a fluidic system (5) for receiving the filtered sample (2), the fluidic system (5) including: (i) a receiving opening (8) arranged at least substantially centrally under the membrane (3) for receiving the filtered sample (2), and (ii) an elevated region (9) of the carrier (4) extending upwardly toward and supporting the membrane (3), and extending at least partially annularly around the receiving opening (8),
 a cover (6) overlying the carrier (4), and including an annular opening into which the elevated region (9) of the carrier (4) extends, where the membrane (3) rests loosely on the cover (6),
 a receiving device (14) overlying the cover and the membrane (3) and operating to receive and direct the sample (2) to the membrane (3) via capillary action, and
 a conveying device (15) which generates one of negative and positive pressure for acceleration of the filtration of the sample (2) through the membrane (3) only after the filtered sample (2) has at least one of reached and partly filled the fluidic system (5) as a result of capillary forces.

2. The device according to claim 1, further comprising:
 a receiving channel (7) which is formed by an opening in the carrier (4), and which is in fluidic communication with the receiving opening (8) and operates to carry the filtered sample (2) away from the membrane (3),
 wherein the membrane (3) is at least one of: (i) directly connected to the carrier (4) at least one of edges and circumferentially, and (ii) accommodated in a recess (19) of the carrier (4).

3. The device according to claim 1, wherein the carrier (4) comprises a structure (16) facing the membrane (3) for supplying the filtered sample (2) to the receiving opening (8).

4. The device according to claim 1, wherein the membrane (3) rests loosely on the carrier (4) and the cover (6) and is not secured in gas-tight manner.

5. The device according to claim 1, further comprising a feed device (11) for the sample (2) in capillary contact with the membrane (3), wherein the feed device (11) is of funnel-shaped configuration.

6. The device according to claim 5, wherein the feed device (11) is arranged in the receiving device (14), the membrane (3) being connected to the receiving device (14) at least one of edges and circumferentially.

* * * * *